US008375949B2

(12) United States Patent
Shim

(10) Patent No.: US 8,375,949 B2
(45) Date of Patent: Feb. 19, 2013

(54) SANITARY MASK FOR THE PROTECTION OF OTHERS

(76) Inventor: Kyu-Sung Shim, Bucheon-si (KR)

( * ) Notice: Subject to any disclaimer, the term of this patent is extended or adjusted under 35 U.S.C. 154(b) by 230 days.

(21) Appl. No.: 12/739,923

(22) PCT Filed: Jan. 3, 2009

(86) PCT No.: PCT/KR2009/000018

§ 371 (c)(1), (2), (4) Date: Apr. 26, 2010

(87) PCT Pub. No.: WO2009/088185

PCT Pub. Date: Jul. 16, 2009

(65) Prior Publication Data

US 2010/0326444 A1 Dec. 30, 2010

(30) Foreign Application Priority Data

Jan. 8, 2008 (KR) ........................ 10-2008-0002195

(51) Int. Cl.
*A61M 11/00* (2006.01)

(52) U.S. Cl. .................................................. 128/206.12

(58) Field of Classification Search . 128/205.29–206.19
See application file for complete search history.

(56) References Cited

U.S. PATENT DOCUMENTS 2,954,027 A * 9/1960 Marasco .................. 128/206.28
6,629,532 B2 * 10/2003 Campbell, Sr. .......... 128/207.11
6,928,657 B2 * 8/2005 Bell et al. .............................. 2/9
7,802,572 B2 * 9/2010 Hahne ...................... 128/206.19
7,856,982 B2 * 12/2010 Matula et al. ............ 128/207.13

FOREIGN PATENT DOCUMENTS

JP 2005-185381 A 7/2005
JP 2007-229279 A 9/2007
KR 20-2000-001194 U 6/2000

* cited by examiner

*Primary Examiner* — Steven Douglas
(74) *Attorney, Agent, or Firm* — IP Legal Services, LLC

(57) ABSTRACT

Disclosed is a sanitary mask for hygienically protecting others that can be conveniently re-used and has a simple structure firmly maintained while the sanitary mask is used, so as to surely achieve the purpose of the sanitary mask, by molding the overall frame of plastics and improving the structure from a structure of preceding Korean Patent Application No. 10-2007-111003, which was filed by the inventor(s) of the present invention before the filing of the present patent application. The sanitary mask for hygienically protecting other people by blocking unsanitary substances provided by respiratory organs including a mouth and a nose of a user from spreading to and contaminating a clean object while exposing the respiratory organs comprising: a lower body molded in a curved shape, i.e., a 'U' shape, and including supporters to be hung on the ears of the user or to be wound around a back head of the user at the ends of both sides of the lower body; and a respiratory organ front cover configured to be inclined upward from an upper portion of a front portion of the lower body and cover a front portion of an area around the respiratory organs of the user to thereby expose the respiratory organs of the user.

12 Claims, 7 Drawing Sheets

*-Prior Art-*

*-Prior Art-*

SANITARY MASK FOR THE PROTECTION OF OTHERS

CROSS REFERENCE TO PRIOR APPLICATIONS

This application is a National Stage Patent Application of PCT International Patent Application No. PCT/KR2009/000018 (filed on Jan. 3, 2009) under 35 U.S.C. 371, which claims priority to Korean Patent Application Nos. 10-2008-0002195 (filed on Jan. 8, 2008), which are hereby incorporated by reference in their entirety.

TECHNICAL FIELD

Exemplary embodiments of the present invention relate to a sanitary mask for hygienically protecting other people that blocks unsanitary foreign substance provided by a respiratory organ from contaminating a clean object such as food while not obstructing breathing or speaking so as to facilitate the sanitation management at a restaurant without inconvenience caused by wearing the sanitary mask. The present invention provides an technology improved from Korean Patent Application No. 10-2007-111003, which was filed by the inventor (s) of the present invention before the filing date of the present patent application. As the entire frame is molded of plastics and the structure is innovatively improved, the sanitary mask according to one embodiment of the present invention has a simple structure, becomes re-usable and convenient in use, and in use, firmly sustains the structure so as to fulfill the purposes of the sanitary mask for hygienically protecting others.

BACKGROUND ART

In general, sanitary masks are used to protect a person who is wearing the sanitary mask from hazardous environmental materials, such as dust at an industrial site or to protect the other objects other than the a person who is wearing the sanitary mask, such as food, from unsanitary substances provided from a human body at a food-related place requiring cleanness.

Most conventional sanitary masks include a mask body for covering a mouth and nose area and strings or loops for fixing the mask body on both sides to be elastically supported by the ears or the head.

Since the conventional sanitary mask contacts the face and directly covers the respiration organs, which include the mouth and nose, which may be also referred to as respiratory organs hereafter, when a person wears the sanitary mask, the person feels stuffy and uncomfortable in breathing and speaking. When the person is a woman, the sanitary mask may be stained with cosmetics such as lipstick, which is quite troublesome.

Due to such problems, people involving in handling or distributing food, who are necessarily required to manage sanitation to hygienically protect others, tend to evade wearing a sanitary mask and thus it is difficult to manage sanitation.

In order to resolve the problems, the inventor(s) of the present invention filed Korean Patent Application No. 10-2007-111003, which will be referred to as a preceding patent application, before the filing of the present patent application. According to the preceding patent application, as illustrated in FIGS. 1 and 2, a sanitary mask 1 includes a body 10 and supporters 30. The body 10 includes a base unit 11 supported by the chin of a user, a screen unit 13 formed to be inclined upward under the respiratory organs from the base unit 11, and a frame sinew unit 17 supporting the screen unit 13 to be inclined. The supporters 30 are formed to be connected to both sides of the body 10 and fixed onto the ears or head of the user. The sanitary mask 1 blocks unsanitary substances provided by the respiratory organs from spreading to and contaminating the others or objects while exposing the mouth and nose of the user.

The sanitary mask of the preceding patent application, filed by the inventor(s) of the present invention, does not obstruct the breathing or speaking by having only the base unit 11 contact and support the chin of a user and having the frame sinew unit 17 support the screen unit 13 to be positioned apart under the respiratory organs, in order words, by not covering the mouth or nose.

Therefore, even with the sanitary mask 1, there is no inconvenience and even a woman wears the sanitary mask 1, the sanitary mask 1 is not stained with cosmetics such as lipstick. Also, since the screen unit 13 is formed to be inclined upward under the respiratory organ areas, unsanitary substances provided by the respiratory organs are kept away from spreading and falling down, and there is an advantage in that people involving in a place where sanitation for hygienically protecting other people is important, such as the kitchen or distribution of restaurant businesses, can easily provide sanitary food and service.

Despite the advantage, however, the preceding patent application, filed by the inventor(s) of the present invention, has an inconvenience in that the frame sinew unit 17 is needed to support the screen unit 13 to be inclined upward, because the body 10 of the sanitary mask 1 integrated with the screen unit 13 is formed of any one selected from the group consisting of fiber, nonwoven, paper, or a combination thereof.

The frame sinew unit 17 includes elastic wires which are formed of an instantly moldable material or resin, which means a material deformed as it is touched by hands, such as a band-type aluminum thin film, and maintaining the deformed state as long as further external force is not applied thereto. When the instantly moldable material is used, the shape of the screen unit 13 is readily distorted even by small external impact and the appearances are damaged. Also, since the screen unit 13 may stick to the respiratory organs as the screen unit 13 is distorted, the user has to take the screen unit 13 away from the respiratory organs with a hand, which is inconvenient.

When the user touches the screen unit 13 with a contaminated hand to restore the screen unit 13 into its original shape, the entire surface of the sanitary mask 1 may become dirty and in this case, the user has to replace the sanitary mask 1 with a new one.

Moreover, to put the frame sinew unit 17 into the body 10, the frame sinew unit 17 may be directly inserted into the inside of the body 10 which is formed in more than two folds or bonded with the body 10.

Furthermore, the sanitary mask 1 suggested in the preceding patent application filed by the inventor(s) of the present invention is a product for a one-time use and it cannot be re-used and a new sanitary mask 1 should be purchased whenever it needs to be used.

DISCLOSURE OF INVENTION

An embodiment of the present invention is directed to a sanitary mask for hygienically protecting others that can be conveniently re-used and has a simple structure firmly maintained while the sanitary mask is used, so as to surely achieve the purpose of the sanitary mask, by molding the overall frame of plastics and improving the structure from a structure of preceding Korean Patent Application No. 10-2007-111003, which was filed by the inventor(s) of the present invention before the filing of the present patent application.

In accordance with an embodiment of the present invention, an sanitary mask for hygienically protecting other people by blocking unclean substances provided by respiratory organs including a mouth and a nose of a user from spreading to and contaminating a clean object while exposing the respiratory organs includes: a lower body molded in a curved shape, i.e., a 'U' shape, and including supporters to be hung on the ears of the user or to be wound around a back head of the user at the ends of both sides of the lower body; and a respiratory organ front cover configured to be inclined upward from an upper portion of a front portion of the lower body and cover a front portion of an area around the respiratory organs of the user to thereby expose the respiratory organs of the user.

Exemplary embodiments of the present invention will be described below in more detail with reference to the accompanying drawings.

Referring to FIGS. 3 to 7, a sanitary mask 1 for hygienically protecting others manufactured in accordance with one embodiment of the present invention is molded of plastics in such a manner that the sanitary mask 1 blocks unsanitary substances provided by respiratory organs from spreading to and contaminating a clean object while exposing the respiratory organs including the mouth and nose of a user wearing the sanitary mask 1. The sanitary mask 1 molded of plastics includes a lower body 100 and a respiratory organ front cover 200. The lower body 100 is molded in a curved shape, i.e., a U shape, and includes supporters 120 to be hung by the ears of a user or to be wound around the back head of the user at the ends of both sides of the lower body 100. The respiratory organ front cover 200 is formed to be inclined upward from the upper portion of the front portion of the lower body 100 and cover the front portion around the respiratory organs of the user, e.g., the mouth and nose of the user, to thereby expose the respiratory organs of the user.

As illustrated in FIGS. 3 to 5, the respiratory organ front cover 200 may be integrated with the upper portion of the front portion of the lower body 100; or as illustrated in FIGS. 6 and 7, the respiratory organ front cover 200 may be formed to include a joining depression 101 on the upper portion of the front portion of the lower body 100 and a joining protrusion 201 in the lower portion of the respiratory organ front cover 200 to be joined with the joining depression 101 so that the respiratory organ front cover 200 could be attached to or detached from the upper portion of the front portion of the lower body 100.

Herein, a chin rest 110 may be formed to be protruded on the internal surface of the front portion of the lower body 100 so that the chin of the user could be comfortably placed.

The respiratory organ front cover 200 may further include sound transmission holes 210 for clearly transmitting the voice of the user to other people.

Also, the respiratory organ front cover 200 may further include a sanitation cover sheet 300, which is formed of any one selected from the group consisting of fiber nonwoven, pulp nonwoven, fiber woven, and pulp woven, as illustrated in FIG. 8. The sanitation cover sheet 300 may be a pocket-type sanitation cover sheet **300*a*, and the lower portion of pocket-type sanitation cover sheet 300*a* is open like a pocket and the pocket-type sanitation cover sheet 300*a* may be put on the respiratory organ front cover 200, or the sanitation cover sheet 300 may be formed in such a manner that a simple sanitation cover sheet 300*b* cut in a predetermined size is put onto the internal surface of the respiratory organ front cover 200** and used.

Also, referring to FIG. 9, the lower body 100 molded in the curved shape, e.g., U shape, is formed to have both sides further diverged outwardly as it goes from the front portion to the rear portion. Since the lower body 100 is flexible, the both sides may be elastically widened or closed to the left and right.

Meanwhile, the supporters 120 may be formed in an inverted 'C'-shaped ear rings 121 by bending the ends of both sides of the lower body 100 molded in a curved 'U' shape, as illustrated in FIG. 10, so that the ends of both sides of the lower body 100 could be hung by the ears of the user. Also, as illustrated in FIG. 11, the supporters 120 may be formed as loop-type ear rings 122 by forming loops at the ends of both sides of the lower body 100 molded in the curved 'U' shape so that the ends of both sides of the lower body 100 could be hung by the ears of the user.

Also, as illustrated in FIG. 12, the supporters 120 may be formed as a fastening band 123 by forming loops at the ends of both sides of the lower body 100 molded in the curved 'U' shape so that the ends of both sides of the lower body 100 could be wound around the back head of the user.

Meanwhile, as illustrated in FIG. 13, the sanitary mask 1 may have an anti-biotic property, deodorization property, and aromatic property by doping, dipping or spraying a functional composition prepared by mixing one or more materials selected from the group consisting of an anti-biotic agent, a deodorizing agent, and an aromatic that are not harmful to a human body, onto the respiratory organ front cover 200 or the sanitation cover sheet 300, and drying the functional composition to thereby form a functional composition layer 400.

EMBODIMENTS

Figure 1:
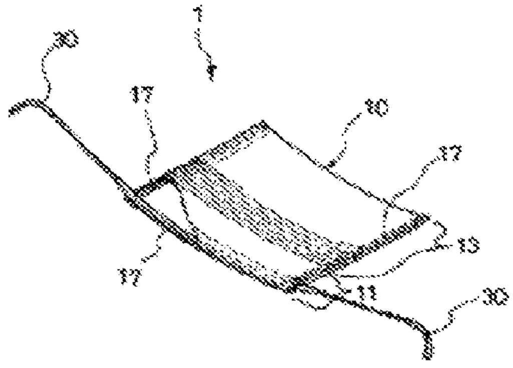
FIG. 1 is a partially sectional view illustrating a sanitary mask in accordance with a preceding invention filed by the inventor(s) of the present invention.
Figure 2:
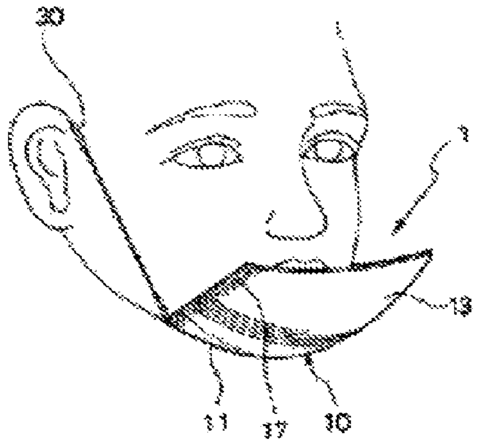
FIG. 2 illustrates the sanitary mask of FIG. 1 worn by a user.
Figure 3:
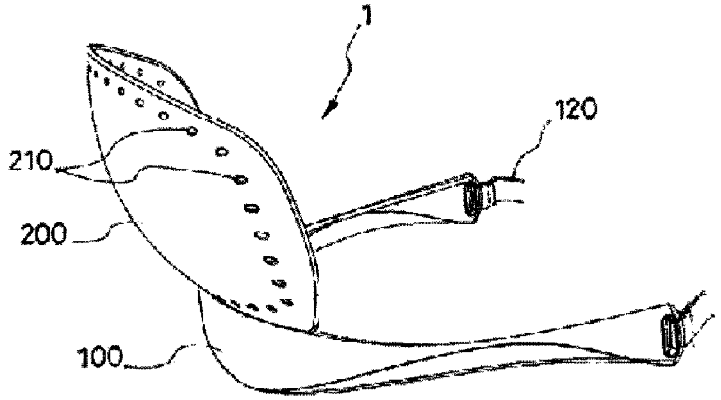
FIG. 3 is a front perspective view illustrating an integrated sanitary mask in accordance with one embodiment of the present invention.
Figure 4:
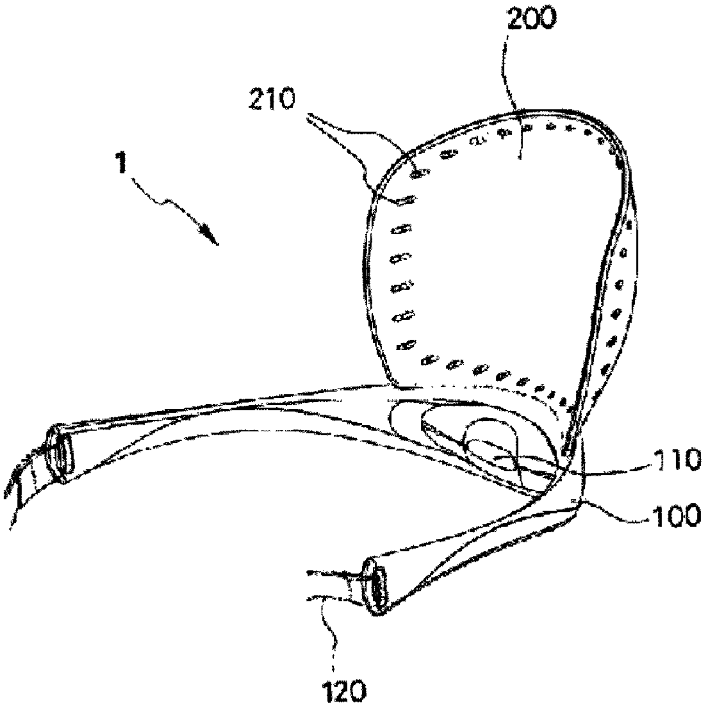
FIG. 4 is a rear perspective view illustrating the integrated sanitary mask in accordance with the embodiment of the present invention.
Figure 5:
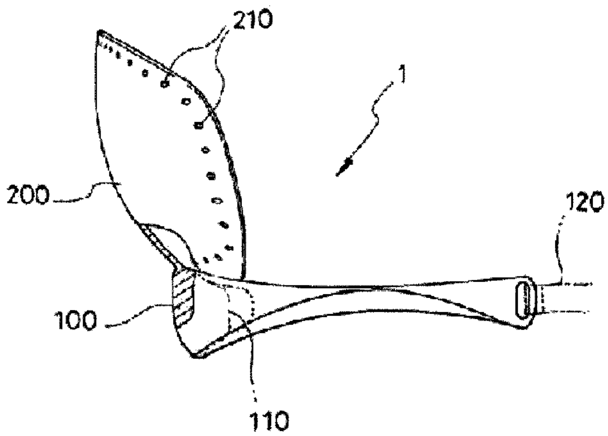
FIG. 5 is a side view illustrating the integrated sanitary mask part of which is cut out in accordance with the embodiment of the present invention.
Figure 6:
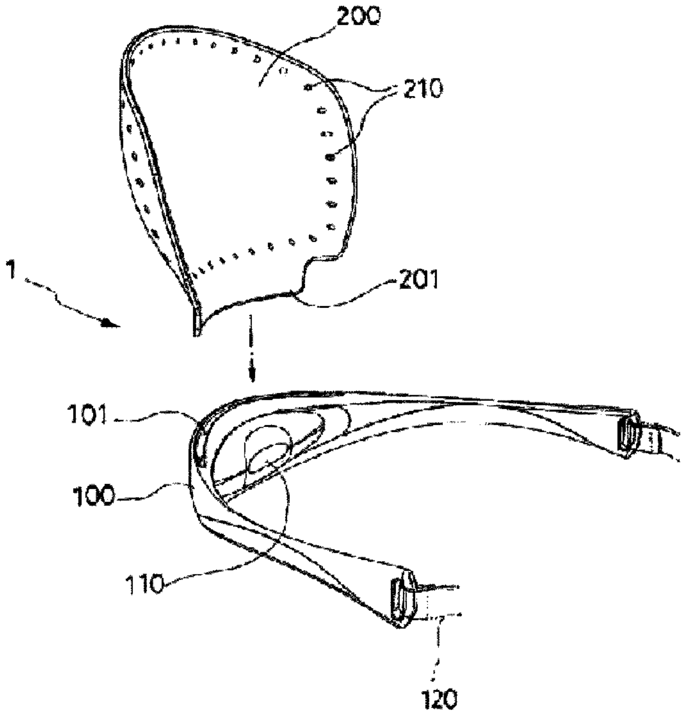
FIG. 6 is a rear perspective view illustrating a disassembled state of a separable sanitary mask in accordance with another embodiment of the present invention.
Figure 7:
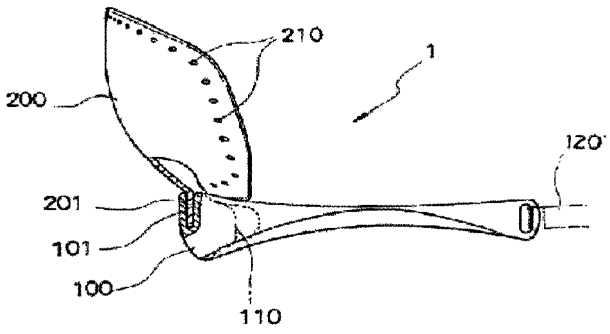
FIG. 7 is a rear perspective view illustrating an assembled state of the separable sanitary mask in accordance with the embodiment of the present invention.
Figure 8:
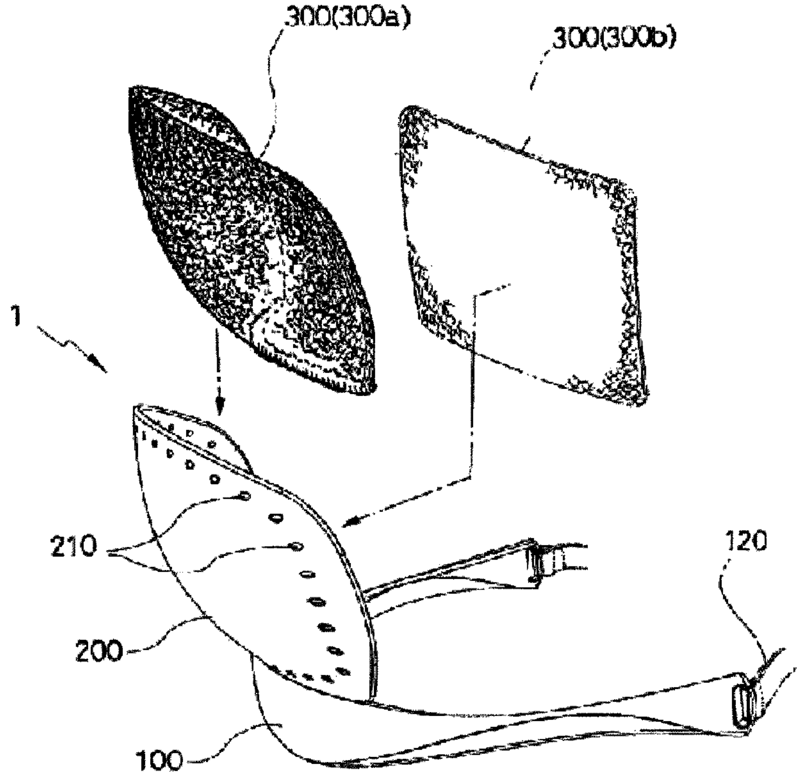
FIG. 8 illustrates a pocket-type sanitation cover sheet in accordance with one embodiment of the present invention.
Figure 9:
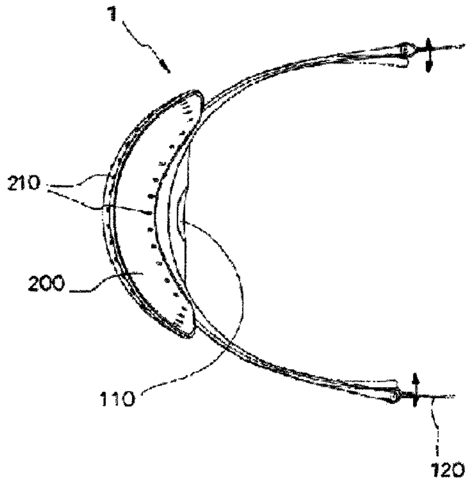
FIG. 9 illustrates a structure for both sides of a lower body in accordance with one embodiment of the present invention.
Figure 10:
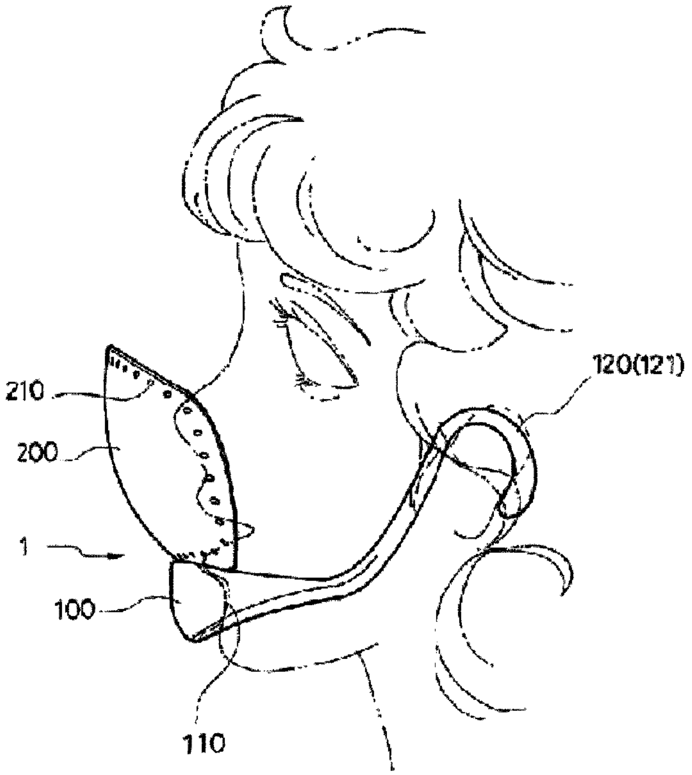
FIG. 10 illustrates supporters formed of an inverted 'C'-shaped ear rings.
Figure 11:
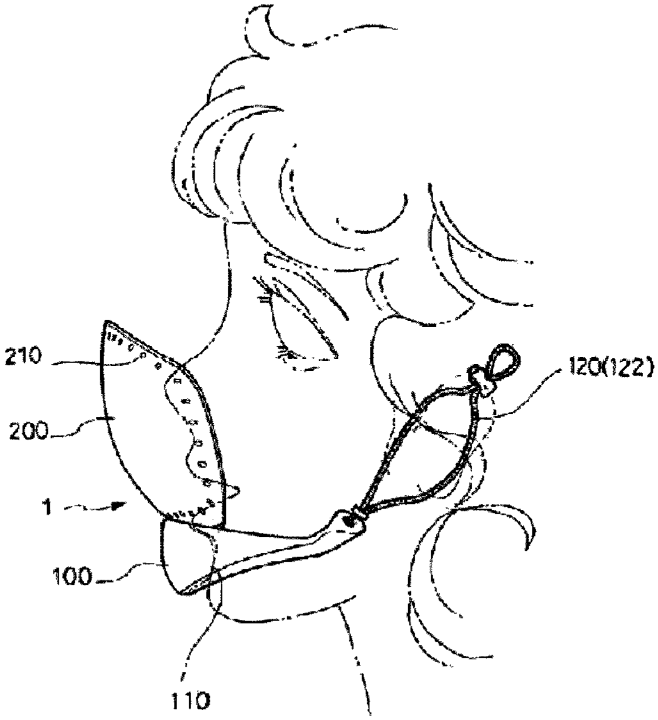
FIG. 11 illustrates supporters formed of a loop-type ear rings.
Figure 12:
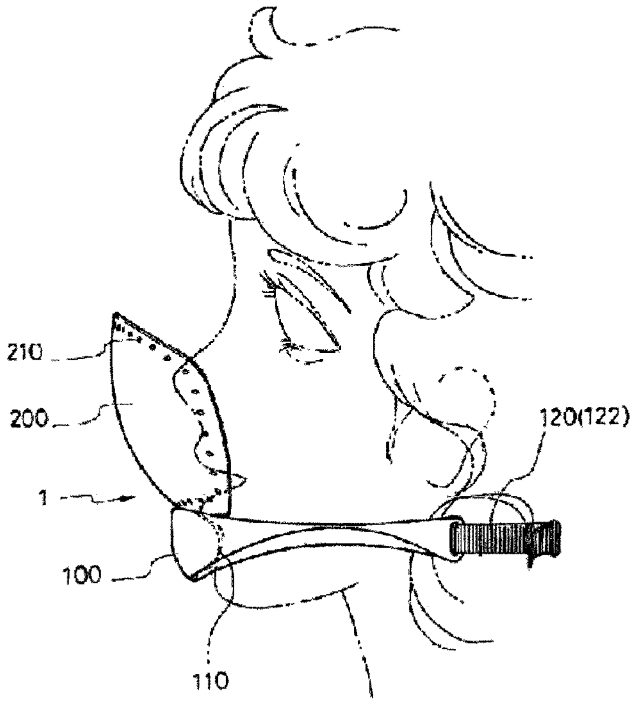
FIG. 12 illustrates supporters formed of a fastening band.
Figure 13:
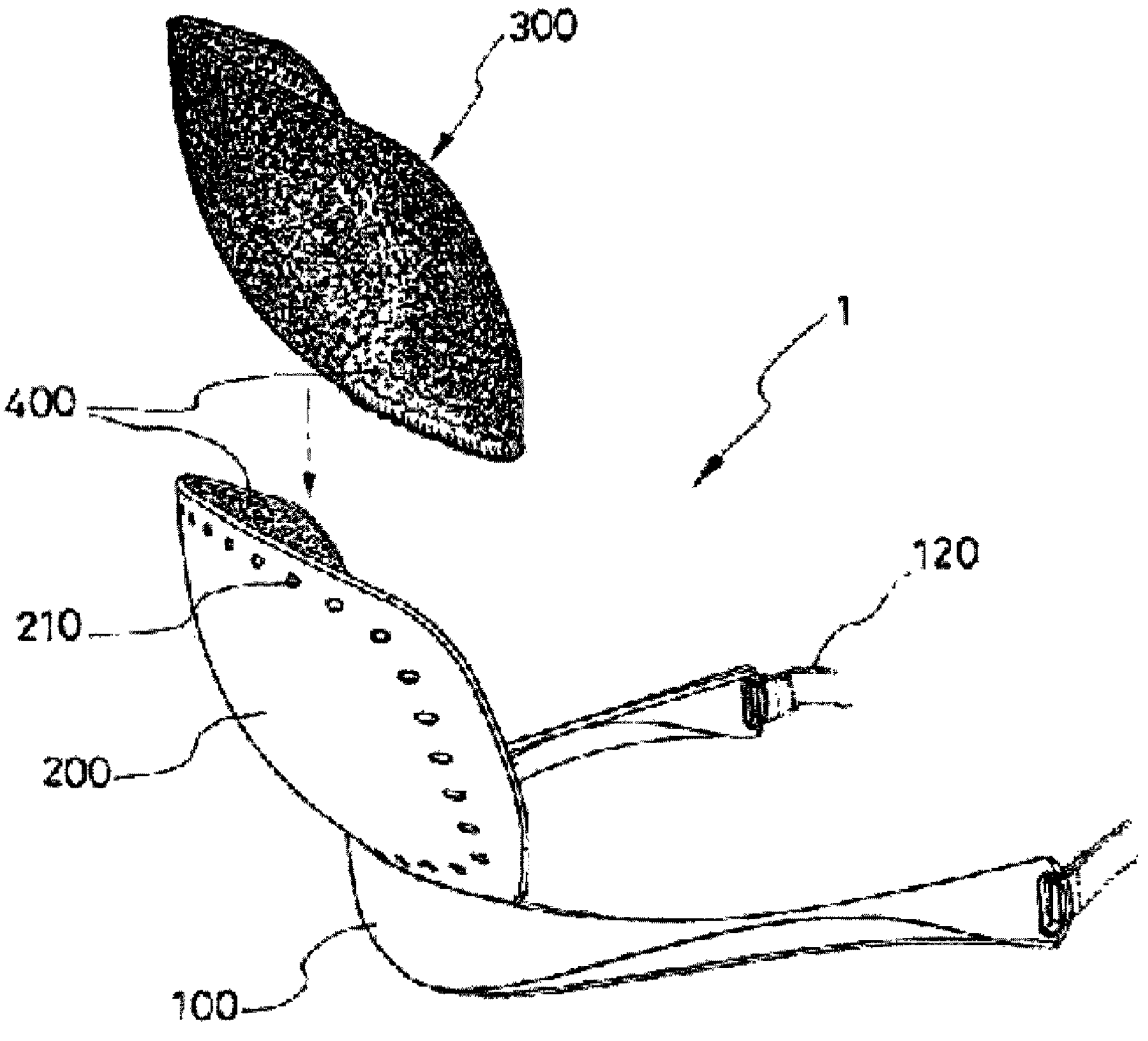
FIG. 13 is a perspective view illustrating a respiratory organ front cover body or a pocket-type sanitation cover sheet with a functional composition layer formed therein.

Hereafter, how a sanitary mask for hygienically protecting others manufactured in accordance with one embodiment of the present invention is used will be described.

First, when a user wears a sanitary mask 1 for hygienically protecting others manufactured according to one embodiment of the present invention, the chin of the user is tightly placed on the internal side surface of the front portion of a lower body 100 molded in a curved 'U' shape, and the ends of both sides of the lower body 100 are hung by the ears of a user or wound around the back head of the user by diverse forms of supporters 120 employed by the lower body 100 while being elastically positioned in the facial sides of the user.

Since the respiratory organ front cover 200 is formed to be inclined upward from the upper portion of the front portion of the lower body 100, the respiratory organ front cover 200 does not directly contact the respiratory organs. Since the respiratory organ front cover 200 is positioned apart from the respiratory organs by a predetermined distance, the respiratory organs are naturally exposed.

Therefore, the user does not feel uncomfortable in breathing or speaking although the user wears the sanitary mask 1 and also since unsanitary substances provided by the respiratory organs are blocked off by the respiratory organ front cover 200, the unsanitary substances does not spread or falling down onto other people or food.

According to the embodiment of the present invention, since the lower body 100 and the respiratory organ front cover 200 of the sanitary mask 1 are all molded of plastics, the sanitary mask 1 is easily manufactured in mass and has excellent quality and appearances. Also, the sanitary mask 1 can firmly maintain the original shape without being deformed by external impact during the use. In addition, the sanitary mask 1 is not a product for a one-time use but it may be washed after being used and repeatedly used.

Besides, when a chin rest 110 is formed on the internal side surface of the front portion of the lower body 100, the chin of the user is brought to a close contact to the chin rest 110. Thus, it is easily for the user to wear the sanitary mask 1. Once the user wears the sanitary mask 1, the user feel comfortable because the sanitary mask 1 fits to the chin of the user. The chin rest 110 also prevents the unsanitary substances from spreading and falling down to the lower portion of the chin rest 110 and prevents the lower body 100 from easily moving or getting off from the chin.

When sound transmission holes 210 are formed in the respiratory organ front cover 200, the voice of the user is clearly transmitted to other people through the sound transmission holes 210.

Also, when the respiratory organ front cover 200 is combined with a sanitation cover sheet 300, which is formed of any one selected from the group consisting of fiber nonwoven, pulp nonwoven, fiber woven, and pulp woven, the used sanitation cover sheet 300 may be separated and replaced with a new one, which makes the sanitary mask 1 of the present invention more hygienic.

Meanwhile, the lower body 100 molded in a curved ' U' shape has its ends of both sides widened outwardly as it goes from the front portion to the rear portion. Since the lower body 100 is flexible, it can be elastically widened or closed to the left and right so that the user could easily wear the sanitary mask 1 regardless of the face size or facial curved form of the user. Also, once the user wears the sanitary mask 1, the sanitary mask 1 comfortably fits into the face of the user so that the user could act freely while wearing the sanitary mask 1.

Herein, the ends of both sides of the lower body 100 molded in a curved 'U' shape include diverse forms of supporters 120. In particular, when rings are formed at the ends of both sides of the lower body 100 and a fastening band 123 are formed therein, the sanitary mask 1 winds around the back head of the user and gets fixed onto the head of the user, the fixation is firm and stable even when the user moves.

Meanwhile, the sanitary mask 1 may have an anti-biotic property, deodorization property, and aromatic property when a functional composition layer 400 is formed by doping, dipping or spraying the functional composition prepared by mixing one or more materials selected from the group consisting of an anti-biotic agent, a deodorizing agent, and an aromatic that are not harmful to a human body onto the respiratory organ front cover 200 or the sanitation cover sheet 300, and drying the functional composition. Therefore, the user can become more sanitized, stable, and comfortable and thereby concentrate on the work.

To sum up, the technology in accordance with one embodiment of the present invention not only achieves the purposes of preceding Korean Patent Application No. 10-2007-111003, filed by the inventor(s) of the present invention, which are to prevent unsanitary substances provided by the respiratory organs from contaminating an object which is supposed to be clean, such as food, and facilitate sanitation management at a restaurant business by eliminating the uncomfortableness while not obstructing such basic actions as breathing and speaking; but also provides diverse advantages by molding the overall frame of the sanitary mask 1 of plastics and improving the structure remarkably. The advantages include simple structure, easy manufacturing, fine appearances, convenient use, firm shape that is not deformed by external impact during the use, and repeated use instead of one-time use.

What is claimed is:

1. An sanitary mask for hygienically protecting other people by blocking unsanitary substances provided by respiratory organs including a mouth and a nose of a user from spreading to and contaminating a clean object while exposing the respiratory organs comprising:

a lower body molded in a curved shape, and including at least one of i) supporters to be hung on the ears of the user and ii) supporters to be wound around a back head of the user at the ends of both sides of the lower body; and a respiratory organ front cover configured to be inclined upward from an upper portion of a front portion of the lower body and cover a front portion of an area around the respiratory organs of the user to thereby expose the respiratory organs of the user.

2. The sanitary mask according to claim 1, wherein the respiratory organ front cover is integrated with the upper portion of the front portion of the lower body.

3. The sanitary mask according to claim 1, wherein a joining depression is formed in the upper portion of the front portion of the lower body and a joining protrusion is formed in at least one of:

i) a lower portion of the respiratory organ front cover to be joined with the joining depression so that the respiratory organ front cover is attached to the upper portion of the front portion of the lower body, and ii) a lower portion of the respiratory organ front cover to be joined with the joining depression so that the respiratory organ front cover is detached from the upper portion of the front portion of the lower body.

4. The sanitary mask according to claim 1, further comprising:

a chin rest configured on an internal surface of the front portion of the lower body to fit to a chin of the user.

5. The sanitary mask according to claim 1, wherein the respiratory organ front cover further comprises sound transmission holes to clearly transmit voice of the user to other people.

6. The sanitary mask according to 1, wherein the respiratory organ front cover further comprises:

a sanitation cover sheet formed of one selected from the group consisting of fiber nonwoven, pulp nonwoven, fiber woven, and pulp woven.

7. The sanitary mask according to claim 1, wherein the lower body molded in a curved shape has the ends of both sides more widened outwardly in the rear portion than in the front portion and since the lower body is flexible, the ends of both sides of the lower body are elastically widened or closed to left and right sides.

8. The sanitary mask according to claim 1, wherein the supporters are inverted ‘C’-shaped ear rings formed by bending the ends of both sides of the lower body molded in the ‘U’ shape and hung on the ears of the user.

9. The sanitary mask according to claim 1, wherein the supporters are loop-type ear rings formed by forming loops at the ends of both sides of the lower body molded in the curved ‘U’ shape and hung on the ears of the user.

10. The sanitary mask according to claim 1, wherein the supporters are a fastening band formed by forming loops at the ends of both sides of the lower body molded in the curved ‘U’ shape and wound around the back head of the user.

11. The sanitary mask according to claim 1, wherein the respiratory organ front cover includes a functional composition layer by at least one of doping, dipping and spraying, a functional composition prepared by mixing, one or more materials selected from the group consisting of an anti-biotic agent, a deodorizing agent, and an aromatic that are not harmful to a human body, and drying the functional composition to thereby have an anti-biotic property, deodorization property, and aromatic property.

12. The sanitary mask according to claim 6, wherein the sanitation cover sheet includes a functional composition layer by at least one of doping, dipping and spraying a functional composition prepared by mixing one or more materials selected from the group consisting of an anti-biotic agent, a deodorizing agent, and an aromatic that are not harmful to a human body, and drying the functional composition to thereby have an anti-biotic property, deodorization property, and aromatic property.

* * * * *